United States Patent [19]

Gerhart et al.

[11] Patent Number: 5,286,763

[45] Date of Patent: Feb. 15, 1994

[54] BIOERODIBLE POLYMERS FOR DRUG DELIVERY IN BONE

[75] Inventors: Tobin N. Gerhart, Brockline; Cato T. Laurencin, Somerville, both of Mass.; Abraham J. Domb, Baltimore, Md.; Robert S. Langer, Newton; Wilson C. Hayes, Lincoln, both of Mass.

[73] Assignee: Massachusetts Institute of Technology, Cambridge, Mass.

[21] Appl. No.: 908,438

[22] Filed: Jun. 30, 1992

Related U.S. Application Data

[63] Continuation of Ser. No. 810,324, Dec. 19, 1991, abandoned, which is a continuation of Ser. No. 690,042, Apr. 23, 1991, abandoned, which is a continuation of Ser. No. 361,222, Jun. 5, 1989, abandoned, which is a continuation-in-part of Ser. No. 613,001, May 21, 1984, Pat. No. 4,906,474, which is a continuation of Ser. No. 477,710, Mar. 22, 1983, abandoned, said Ser. No. 361,222, is a continuation-in-part of Ser. No. 61,294, Jun. 12, 1987, Pat. No. 4,888,176, which is a continuation-in-part of Ser. No. 892,809, Aug. 1, 1983, Pat. No. 4,757,128, which is a continuation-in-part of Ser. No. 613,001, Aug. 1, 1983, Pat. No. 4,906,474, said Ser. No. 361,222, is a continuation-in-part of Ser. No. 313,953, Feb. 22, 1989, abandoned.

[51] Int. Cl.$^5$ ............... A61M 31/00; C08G 63/02
[52] U.S. Cl. ............... 514/772.4; 424/426; 523/113; 523/115; 528/271; 528/354; 604/891.1; 514/30; 514/40
[58] Field of Search ........... 528/354, 271; 623/16; 424/426, 409, 78; 523/113, 115; 514/772.3; 604/891.1

[56] References Cited

U.S. PATENT DOCUMENTS

| | | | |
|---|---|---|---|
| 3,887,699 | 6/1975 | Yolles | 424/426 |
| 3,991,766 | 11/1976 | Schmitt et al. | 424/426 |
| 4,419,340 | 12/1983 | Yolles | 424/426 |
| 4,563,489 | 1/1986 | Wrist et al. | 524/21 |
| 4,612,009 | 9/1986 | Drobnik et al. | 424/426 |
| 4,675,189 | 6/1987 | Kent et al. | 424/426 |
| 4,797,282 | 1/1989 | Wahlig et al. | 424/422 |
| 4,806,621 | 2/1989 | Kohn et al. | 523/113 |
| 4,832,686 | 5/1989 | Anderson | 424/426 |
| 4,906,474 | 3/1990 | Langer et al. | 424/428 |
| 5,122,367 | 6/1992 | Ron et al. | 424/80 |

*Primary Examiner*—John Kight, III
*Assistant Examiner*—Shelley A. Dodson
*Attorney, Agent, or Firm*—Kilpatrick & Cody

[57] ABSTRACT

Bioerodible polymers which degrade completely into nontoxic residues over a clinically useful period of time, including polyanhydrides, polyorthoesters, polyglycolic acid, polylactic acid, and copolymers thereof, are used for the delivery of bioactive agents, including antibiotics, chemotherapeutic agents, inhibitors of angiogenesis, and simulators of bone growth, directly into bone.

8 Claims, No Drawings

BIOERODIBLE POLYMERS FOR DRUG DELIVERY IN BONE

BACKGROUND OF THE INVENTION

This is a continuation of copending application Ser. No. 07/810,324 filed on Dec. 19, 1991, now abandoned, which is a continuation of U.S. Ser. No. 07/690,042 filed Apr. 23, 1991, now abandoned which is a continuation of U.S. Ser. No. 07/361,222 filed Jun. 5, 1989, now abandoned, which is a continuation-in-part of U.S. Ser. No. 613,001 entitled "Bioerodible Polyanhydrides for Controlled Drug Delivery" filed May 21, 1984, now U.S. Pat. No. 4,906,474, by Robert S. Langer, Howard Rosen, Robert J. Linhardt, and Kam Leong, which is a continuation of U.S. Ser. No. 477,710 filed March 22, 1983, now abandoned; Ser. No. 361,222 is a continuation-in-part of U.S. Ser. No. 061,294 entitled "Controlled Drug Delivery High Molecular Weight Polyanhydrides" filed Jun. 12, 1987, now U.S. Pat. No. 4,888,176, by Robert S. Langer, Edith Mathiowitz, Abraham J. Domb, and Cato T. Laurencin, which is a continuation-in-part of U.S. Ser. No. 892,809 filed Aug. 1, 1986, issued as U.S. Pat. No. 4,757,128 Jul. 12, 1988, which is a continuation-in-part of U.S. Ser. No. 613,001 now U.S. Pat. No. 4,906,474; and Ser. No. 361,222 is a continuation-in-part of U.S. Ser. No. 313,953 entitled "Delivery System for Controlled Release of Bioactive Factors" filed Feb. 22, 1989, now abandoned, by Cato T. Laurencin, Paul A. Lucus, Glenn T. Syftestad, Abraham J. Domb, Julia Glowacki, and Robert S. Langer.

This relates to a method and polymeric compositions for treatment of infection in bone.

Osteomyelitis, both in its acute and chronic forms, remains a difficult disease entity to treat. In acute osteomyelitis, a rapidly progressing infection of bone takes place, with involvement of the medullary space, cortex, or periosteum. The chronic form of osteomyelitis consists of a more longstanding type of bone infection characterized by low-grade inflammation, sequestra (areas of dead bone), involucra (shells of cortical bone resulting from periosteal elevation due to an inflammatory focus), fistula and bone sclerosis. Three basic mechanisms by which osteomyelitis occurs have been identified: hematogenous spread, spread from a contiguous focus (such as sinuses and teeth), and direct bacterial seeding as a result of trauma, or operative procedure.

The microorganism most often responsible for clinical infections is *Staphylococcus aureus*. Antibiotics have continued to be the mainstay of treatment for osteomyelitis. However, clinical infections can be difficult to eradicate, and it is estimated that as many as 15% to 30% of acute osteomyelitis cases are complicated by persistence of infection. Moreover, in most cases, chronic osteomyelitis can only be treated using surgical debridement in combination with antibiotic therapy. Even with surgery, eradication of the disease is not assured.

The drawbacks in conventional antibiotic therapy to bone are manifold. With the exception of the fluorinated quinolones, bone tissue levels of antibiotics are never greater than 30% of corresponding peak serum levels. Accordingly, the systemic levels of antibiotics used to treat infections can result in serious toxicity to various organ systems. Further, in conventional therapy, antibiotics must be administered for many weeks in order to effect a cure. Costs to the health care system and to society for close monitoring of intravenous antibiotic therapy in the hospital or outpatient setting, for expensive antibiotics which are excreted before reaching the diseased bone, and for morbidity and mortality due to failure of eradication of disease are considerable.

Controlled local release from implanted carriers has been advocated as a technique for achieving high local antibiotic concentrations while maintaining low systemic levels. Polymethylmethacrylate (PMKA) bone cement loaded with antibiotics has been used clinically since 1970, principally for fixation of hip replacement components to bone. Numerous in vitro, animal, and human studies have measured effective local release of antibiotics by PMMA. See, for example, Bayston, et al., *J.Bone Joint Surg.* 64B, no. 4, 460–464 (1982); Buchholz, et al., *Chirurgic.* 41, 511–514 (1970); Buchholz, et al., *Clin. Orthop.* 190, 96–108 (1984); Trippel, *J. Bone Joint Surg.* 68-A(8), 1297–1302 (1986).

When used prophylactically, such as in hip arthroplasty patients, PMMA mixed with antibiotics is injected in moldable form and allowed to harden in vivo. The risk of a persistent infection is low, and the prosthetic components require the cement for stabilization. However, because PMMA is inert and acts as a foreign body, a second surgical procedure is required for its removal in established infections. Thus, for treatment of osteomyelitis, PMMA is first formed into beads to facilitate subsequent removal several weeks after implantation, as described by Majid, et al., *Acta. Orthorp. Scand.* 56, 265–268 (1985) and Vecsei, et al., *Ciin. Orthop.* 159, 201–207 (1981). The size and fixed shape of the beads keeps them from penetrating into the smaller interstices of the wound cavity, and thus undesirably lengthens the diffusion path that antibiotics must travel in order to reach the infected tissue.

In order to avoid the drawbacks inherent with PMMA when treating established infections, biodegradable materials such as plaster of paris and bone graft have been proposed for use as carrier materials for antibiotics (Mackey, et al., *Clin. Orthop.* 167, 263–268 (1982); McLaren, et al., *Transactions of the 12th Annual Meeting of the Society for Biomaterials*, Minneapolis-St.Paul, Minn. 102 (May 29–Jun. 1, 1986). These would require no second procedure for removal, and could permit more intimate and complete filling of the wound cavity.

Gerhart, et al., described in *J. Orthop. Res.* 6,585–592 (1988), the use of a biodegradable polypropylenefumarate-methylmethacrylate (PPF-MMA) bone cement for controlled release of Antibiotics in an in vivo model. This cement is initially moldable and polymerizes in vivo, and could potentially supply some structural support prior to degrading. However, there is the problem of residual toxic methacrylate monomer being released as the bone cement degrades. Further, not only is there only about 15% resorption of the polymer over a period of three months, but studies have not shown any greater effectiveness in using the biodegradable polymer over using polymethylmethacylate.

It is therefore an object of the present invention to provide biodegradable compositions, and methods for use thereof, for controlled administration of bioactive materials to bone.

It is a further object of the present invention to provide biodegradable compositions which completely degrade in vivo over a physiologically useful period of time into completely non-toxic residues.

It is another object of the present invention to provide compositions which show greater clinical efficacy in the treatment of bone disease, as compared to conventional localized treatment.

SUMMARY OF THE INVENTION

Bioerodible polymers which degrade completely into nontoxic residues over a clinically useful period of time, including polyanhydrides, polyorthoesters, polyglycolic acid, polylactic acid, and copolymers thereof, are used for the delivery of bioactive agents, including antibiotics, chemotherapeutic agents, inhibitors of angiogenesis, and simulators of bone growth, directly into bone. The preferred polymers are polyanhydrides.

In one example, polyanhydride copolymers were used for the treatment of clinical infections in long bones. Rats were quantitatively infected with a virulent strain of *Staphylococcus aureus.* Using a 50:50 copolymer of bis-carboxyphenoxy propane and sebacic acid, [p(CPP-SA) 50:50], 10% loaded with gentamicin sulfate, tibias were inoculated with bacteria, then implanted with bioerodible polymer containing antibiotic. After 10 weeks, rats were sacrificed and remaining bacteria were measured. The bioerodible polyanhydride delivery system effectively treated the osteomyelitis with results showing significantly greater levels of bacteria reduction in tibia than conventional systems of gentamicin delivery in bone using polymethylmethacrylate or polypropylene fumarate-methylmethacrylate bone cements.

DETAILED DESCRIPTION OF THE INVENTION

A method and compositions for the controlled delivery of bioactive molecules to bone is based on the use of biodegradable, biocompatible polymers in combination with the bioactive molecules to achieve both efficacious release of molecules and removal of the polymer from the treatment site within a physiologically useful time period.

A variety of polymers can be used to form the implant for purposes of delivering bioactive molecules to bone. The polymers must be biocompatible. As used herein, biocompatible means that the polymer is non-toxic, non-mutagenic, elicits minimal to moderate inflammatory reaction, and completely degrades in a controlled manner into non-toxic residues. In the preferred embodiment, surface erodible polymers such as polyanhydrides or polyorthoesters are used. Alternatively, other polymers such as polylactic acid and polyglycolic acid can also be used. The composition of the polymer, as well as the molecular weight and physical properties, can be varied according to the application. For example, more hydrophobic polyanhydrides can be used where it is desirable to increase the time of degradation. Compounds can be mixed into or polymerized with the polymer as required for additional strength or other desirable physical properties, using materials known to those skilled in the art from studies involving bone cements. For example, tricalicum phosphate or other ceramic type materials that provide increased physical strength can be added to the composition.

In general, for repair of bone breaks, the polymer should release material over a period of approximately four to twelve weeks (generally twelve weeks in a human for sufficient repair to occur for the bone to become weight bearing). The polymer should also degrade completely over a period no longer than about sixteen to twenty weeks. Release and degradation times for treatment of bone tumors and infections have to be determined on an individual basis. The time will depend in part upon what materials are to be released from the polymer.

Many polymers are biodegradable if left in vivo for a sufficiently long period of time. Others have such a long period for degradation that they are not generally termed "biodegradable". Polymethylmethacrylate (PMMA) is not biodegradable. Polypropylenefumarate - methylmethacrylate is not biocompatible as defined herein due to the presence of toxic unreacted methacrylic acid monomers, nor is it generally biodegradable within a physiologically meaningful time, since only 15% of the polymer is resorbed within three months. Further, neither polymer effects controlled release. Ethylene vinyl acetate is also of limited value since it degrades over a period of as long as four years for a relatively thin disk.

The polymers can be mixed with or used to encapsulate the bioactive molecules using methods known to those skilled in the art, including mixing polymer particles and compressing, solvent casting, and microencapsulation within polymer in combination with a matrix for delivery. Examples of useful bioactive molecules include antibiotics such as gentamicin and vancomycin, bone morphogenic factors, bone growth factors such as $IGF_1$, and compounds for treatment of bone tumors, such as angiogenesis inhibitors and chemotherapeutic agents. The polymers such as the polyanhydrides are particularly well adapted for delivery of molecules such as the water soluble molecules described in co-pending U.S. Ser. No. 313,953, entitled "Delivery System for Controlled Release of Bioactive Factors", filed February 1989 by Cato T. Laurencin, Paul A. Lucas, Glenn T. Syftestad, Abraham J. Domb, Julia Glowacki, and Robert S. Langer.

The polymeric delivery devices have many advantages over the prior art bone cements, PMMA-drug implants, and systemic administration of antibiotics or chemotherapeutic agents. The release is much more site-specific. Release occurs in a controlled manner over a predetermined period of time. Compounds can be delivered in combination, even using different types of polymers having staggered degradation times to effect release of the compounds in a particular sequence. The devices completely degrade over relatively short times, ranging from days to a few weeks or months, into non-toxic residues. Fillers and modifications of chemical composition can be used to enhance the strength of the polymer and therefore facilitate restoration of weight bearing capacity. Polymer can be used to fill space and encourage bone growth while inhibiting vascularization or reoccurrence of a tumor.

The present invention is further described with reference to the following non-limiting examples.

Osteomyelitis cannot be reliably created in experimental animals unless foreign or necrotic material is present. Investigators have used sodium morrhuate to create a necrotic focus to potentiate bone infections in rabbits and rats. Others have placed foreign bodies such as stainless steel pins in rabbit, or acrylic cement in rat or dog tibias respectively, to establish an infection. A preferred method uses a modification of an animal model described by Elson, et al., to test the effectiveness of antibiotic-loaded cements in animals with established infections as well as in those inoculated immediately before treatment (prophylaxis). High speed drilling of the tibia is used to create a small region of necrosis at an inoculation site. PMMA implants are placed into the drilled holes to act as foreign bodies for three weeks, at which time they are removed. Staphylococcal infection is reliably produced in all animals, as indicated clinically by abscesses and draining sinuses.

EXAMPLE 1

Comparison of PPF-MMA and PMMA Delivery of Antibiotics in the Treatment of Osteomyelitis A biodegradable bone cement containing gentamicin and vancomycin was used both for treatment and prophylaxis of *Staphylococcus aureus* osteomyelitis in rats. Osteomyelitis was established by inoculating *S. aureus* into holes drilled in the proximal tibias with PMMA cylinders implanted for three weeks. The infections were serially evaluated by clinical and radiographic examination, and by quantitative culture for colony forming units (CFU), at time of sacrifice. For treatment, cements containing antibiotic were implanted for 3 weeks. The CFU geometric mean for sites treated with biodegradable cement containing antibiotics (1.7 to 5.4 CFU) were significantly different ($p<0.001$) from controls (2,700 CFU). Prophylactically treated sites developed no clinically apparent infections (0.22 CFU).

The results demonstrate that there were no significant difference in therapeutic effectiveness found between the biodegradable PPF-MMA cement and PMMA (4.4 CFU). The three week treatment period may have been too short to realize the full theoretical advantages of a biodegradable carrier for controlled antibiotic release.

Materials and Methods

Osteomyelitis Model.

*Staphylococcus aureus* osteomyelitis was induced in both right and left proximal tibias of 25 Sprague-Dawley retired male breeder albino rats averaging 600 g in weight. Using aseptic technique and general anesthesia (intraperitoneal sodium pentobarbital, 65 mg/kg), the anteromedial tibial metaphysis was exposed via a 1.5 cm longitudinal incision. The periosteum was split and gently retracted using an periosteal elevator. A hole was drilled through the near cortex and underlying trabecular bone using a high speed drill with a 2 mm carbide burr bit.

A suspension of oxacillin-sensitive *S. aureus* containing $1.0\times10^6$ colony forming units (CFU) per ml, was prepared using the Prompt Inoculation System (No. 6306, 3M, St. Paul, Minn. 55144). Ten microliters were injected into the wound site, resulting in an inoCUIUM of $1.0\times10^4$ CFU. The strain of *S. aureus* had originally been isolated from a patient with osteomyelitis. Immediately following inoculation, a $2\times3$ mm preformed PMMA cylinder with a central 4 mm stainless steel wire (to aid radiographic detection and facilitate later removal) was fitted snugly into the hole to act as a foreign body. The periosteum was closed with a single resorbable suture (6.0 Vicryl, Ethicon, Inc.) to secure the PMMA foreign body implant in position in the drill hole. The distal two-thirds of the skin incision was closed with interrupted resorbable suture (6.0 Vicryl), leaving the proximal one-third of the incision open as a potential site for drainage. Postoperative lateral radiographs were obtained of all tibias. The animals were returned to cage activity for three weeks.

After three weeks all animals had their PMMA foreign body implants removed using general anesthesia and aseptic technique. The clinical appearance of the leg was recorded. Sterile gauze was used to manually wipe away pus from the drill hole surrounding soft tissue, but no formal debridement was performed. Implants were inoculated on blood agar plates and into thioglycollate broth and incubated for 24 hours at 35° in 5% $CO_2$.

Implant Preparation.

The PPF/MMA cement was a composite consisting of a tricalcium phosphate and calcium carbonate particulate phase bound together with a matrix phase of a poly(propylene fumarate) prepolymer (PPF) crosslinked with a monomer methylmethacrylate (MMA). The PPF prepolymer was prepared as a heterogenous mixture of short chains (molecular weight 500–1200) of alternating propylene glycol and fumaric acid subunits joined by an ester linkage. The cement was made by mixing PPF (6 g) with MMA monomer (1 g), resulting in a sticky viscous liquid. To this was added benzoyl peroxide (0.25 g) and the particulate phase which consisted of tricalcium phosphate particles (7.5 g; 30–45 mesh or 355–600 microns in diameter) (Mitre, Inc., Columbus, Ohio 43229) and finely powdered calcium carbonate (7.5 g).

Antibiotics, gentamicin sulfate powder (Sigma, St. Louis, Mo. 63178) and/or vancomycin hydrochloride lyophilized powder (Lederle Laboratories, Pearl River, N.Y. 10965), were added to give a 6.6% final concentration, or a ratio of 4 g antibiotic to 60 g cement. Dimethyl-p-toluidine (DMT) (0.2% by weight) was used to initiate the crosslinking reaction which took place in about three minutes at room temperature. Freshly mixed cement was used in some animals. In other animals preformed cement implants were used in order to have a well-defined geometry and quantity of cement. These were made by packing the cement into Teflon TM molds to form cylindrical specimens 3 mm in diameter by 4 mm in length. For comparison, preformed antibiotic-impregnated polymethylmethacrylate (PMMA) specimens were made using the same ratio of 2 g gentamicin and 2 g vancomycin to 60 g PMMA cent Low Viscosity Bone Cement (Zimmer, Warsaw, Ind. 46580) and the same Teflon TM mold technique.

Experimental Design.

Twenty-six animals with established staphylococcal osteomyelitis in both proximal tibias were selected for study and divided into five groups: four treatment groups and one control group. The control animals simply had the distal two-thirds of their skin incisions closed with interrupted resorbable suture leaving the proximal one-third open for drainage. The treated animals had implants of antibiotic impregnated PMMA or PPF/MMA cement inserted into the osteomyelitic cavities of both tibias. The preformed implants were molded 3 mm diameter$\times$4 mm cylinders allowed to harden prior to use so that a defined geometry and volume was employed. The fresh PPF cement was mixed immediately before use and inserted when still deformable. This achieved better filling of the cavity, but resulted in variable amounts of cement being used. Group one (10 sites) had fresh vancomycin/PPF implants; group two (8 sites) fresh vancomycin-gentamicin/PPF implants; group three (8 sites) preformed vancomycin-gentamicin/PPF implants; group four (10 sites) preformed vancomycin-gentamicin/PMMA implants; and group five (20 sites) were controls with no cement. One animal from group four and another from group five died in the perioperative period leaving 8 sites at time of sacrifice for each of these groups.

Three weeks post therapy (6 weeks after the initial inoculation), all animals were sacrificed by lethal intraperitoneal and intracardiac injection of sodium pentobarbital. Using aseptic technique, the hindlimbs were dismembered and surface disinfected by immersion in 95% ethyl alcohol followed by spraying with povidine-iodine solution, which was allowed to air dry. Using a separate set of sterile instruments for each limb, the tibial infection site was exposed and its appearance recorded. The PMMA and remains of the PPF implants were removed, and a 5 mm segment of bone encompassing the infection site excised for quantitative bacteriological culture. Bone segments were inoculated into 2 ml of trypticase soy broth (TSB). The mixture was vortexed, and serial 10-fold dilutions in TSB were made. A 10 $\mu$l inoculum was subcultured to 5% sheep blood agar plates that were incubated for 24 hours at 35° C. in 5% $CO_2$. Colonies were counted only on those plates with approximately 30-100 colonies.

Prophylactic Treatment.

The previous protocol was modified in order to test the prophylactic effectiveness of antibiotic impregnated PPF cement. During a single operative procedure, both proximal tibias of three animals were drilled and inoculated with S. aureus as described above. Then freshly mixed vancomycin impregnated PPF cement was implanted and the wounds closed. These animals were returned to cage activity for three weeks before sacrifice for quantitative cultures of the tibial sites as previously described.

Results.

Three weeks post incubation with S. aureus and insertion of the PMMA foreign body implant, all animals demonstrated clinical and radiographic signs consistent with established chronic osteomyelitis. All implant sites had abscesses and/or draining sinuses. Cultures of the wound sites and retrieved PMMA implants grew out S. aureus in all cases. Radiographs showed osteolysis surrounding the implant, sequestration, reactive periosteal new bone formation, and healed pathologic fractures.

Six weeks following infection (three weeks after treatment was begun), the original implant sites in the control animals still appeared clinically infected whereas those of the treatment groups did not. Radiographs showed little change over the three week treatment period. All infected sites grew S. aureus except for one site that grew only Enterococcus and another site that grew both S. aureus and Proteus. None of the prophylactically treated animals developed any clinical or radiographic signs of infection.

The results of quantitative cultures for the control, PPF and PMMA antibiotic-impregnated cement treated, and prophylactically treated groups were expressed as colony forming units (CFU) of S. aureus cultured from each implant site. Because these values ranged over several orders of magnitude, a log transformation was used to create a more normal distribution. In order to avoid taking the logarithm of zero, 0.1 (-2.3 when expressed as a natural logarithm) was arbitrarily added to each datum. Under these circumstances, the geometric mean is more representative of the average for each group than the mean or medium.

Using an unblocked Newman-Keal's test, the geometric mean of the control group (2,700 CFU) was significantly different (p<0.001) from that of the prophylactic (0.22 CFU) and treatment (1.66-5.42 CFU) groups.

None of the four treatment groups was significantly different from each other. Similarly, the prophylactic group was not significantly different when compared separately with any of the individual treatment groups. However, when the data from the four treatment groups were pooled and compared to the prophylactic group, a two-tailed Mann-Whitney test gave statistically significant differences (p=0.01).

The results demonstrate that both PMMA and biodegradable cements loaded with antibiotics could effectively prevent the development of infections in the proximal tibias of rats inoculated with S. aureus. This is consistent with the work of others who have used antibiotic-loaded PMMA cement prophylactically. Moreover, we found that antibiotic-loaded PMMA cement had some effectiveness in treating established infections. Colony counts in infected tibias treated with either PMMA or the PPF-MMA cement loaded with antibiotics were two orders of magnitude less than the untreated control. Somewhat unexpectedly, no significant differences were seen between the treatment regimens. The use of freshly prepared PPF-PMMA, however, resulted in the addition of variable amounts of cement and antibiotic to each site, and the surrounding tissue thereby was exposed to the potentially toxic effects of more MMA monomer.

EXAMPLE 2

Comparison of PA and PMMA Delivery of Antibiotics in the Treatment of Osteomyelitis The methods described in Example 1 were used to compare the effectiveness of gentamicin-containing PMMA and polyanhydride (PA) in treatment of rats infected with S. aureus. Rats were divided into four groups as follows: group I, control rats implanted with PMMA for three weeks, with no further treatment; group II, rats implanted with PMMA for three weeks, followed by removal of the implant and implantation of gentamicin PMMA pellets; group III, rats implanted with PMMA for three weeks, followed by implantation of a polyanhydride pellet without antibiotics; and group IV, rats implanted with PMMA for three weeks, followed by removal of the implant and implantation of a polyanhydride with 10% gentamicin pellet.

Rats were operated on as described above. In a first control group, a PMMA cement pellet was implanted in both the right and the left tibia after infection of the site with 10 $\mu$l S. aureus suspension (10,000 CFU per tibia). Two rats died following the surgical procedure. After 3 weeks the pellet was removed. All rats had developed a chronic osteomyelitis. They were sacrificed four weeks after infection and both tibias were harvested. One tibia was crushed and then the bacteria counted, and the other tibia was examined. S. aureus was present in all eight specimens.

Nineteen animals were used for the comparative study. For Group I, a PMMA cement pellet was implanted in both the right and left tibia after infection of the rats with 10,000 CFU S. aureus as described above. For Group II, two PMMA pellets containing 10% gentamicin were implanted in three rats and removed after three weeks. For Group III, polyanhydride, poly(carboxyphenoxypropane-sebacic acid) at a ratio of 50:50 (molar ratio of monomers), p(CPP:SA), was implanted in the right tibia of three rats. For Group IV, implants of the same p(CPP:SA) pellets with 10% gentamicin sulfate added were implanted in the left tibia of the same rats. All pellets were 5 mm long and had a diameter of 3.0 mm. Each pellet had an approximate weight of 44.4±2 mg and contained 10% gentamicin by weight. The results are shown in Table 1.

TABLE 1

Treatment of Chronic Osteomyelitis with Antibiotic Impregnated Bone Cement.

| Animal | Bone | No. of Organisms in Bone | Wt. of Bone (g) | No. of S. aureus/ g of Bone |
|---|---|---|---|---|
| Group I: Control | | | | |
| 10 | L | $1.6 \times 10^3$ | .4522 | $3.54 \times 10^3$ |
| | R | $1.86 \times 10^4$ | .6406 | $2.90 \times 10^4$ |
| 11 | L | $1.98 \times 10^4$ | 5286 | $3.74 \times 10^4$ |
| | R | $4.6 \times 10^3$ | .5473 | $8.4 \times 10^3$ |
| 12 | L | $7.0 \times 10^5$ | .4715 | $1.48 \times 10^6$ |
| | R | $3.3 \times 10^4$ | .7899 | $4.2 \times 10^4$ |
| 16 | L | $2.7 \times 10^4$ | .4052 | $6.66 \times 10^4$ |
| | R | $2.2 \times 10^5$ | .4013 | $5.48 \times 10^5$ |
| Group II: PMMA with Gentamicin | | | | |
| 17 | L | $2.04 \times 10^4$ | .3532 | $5.78 \times 10^4$ |
| | R | $2.68 \times 10^4$ | .3964 | $6.76 \times 10^4$ |
| 18 | L | $2.76 \times 10^4$ $5.8 \times 10^3$ | .4932 | $5.60 \times 10^4$ |
| | R | $1.16 \times 10^4$ $4 \times 10^2$ | .3209 | $3.6 \times 10$ |
| 19 | L | $1.42 \times 10^4$ | .4688 | $3.03 \times 10^4$ |
| | R | $6.8 \times 10^3$ | .5412 | $1.26 \times 10^4$ |
| 21 | L | $1.38 \times 10^5$ | .4784 | $2.88 \times 10^3$ |
| | R | $2 \times 10^1$ | 4240 | $4.72 \times 10^1$ |
| Group III: PA pellet | | | | |
| 27 | L | $1.06 \times 10^5$ | .4430 | $2.39 \times 10^5$ |
| | R | $1.38 \times 10^5$ | .4452 | $3.10 \times 10^5$ |
| 28 | L | $2.24 \times 10^5$ | .7809 | $2.87 \times 10^5$ |
| | R | $2.14 \times 10^4$ | .4841 | $4.42 \times 10^4$ |
| 29 | L | $5.6 \times 10^4$ | 1.0492 | $5.34 \times 10^4$ |
| | R | $7.6 \times 10^3$ | .3251 | $2.34 \times 10^4$ |
| 30 | L | $3.42 \times 10^5$ | 1.0340 | $3.31 \times 10^5$ |
| | R | $1 \times 10^2$ | .5365 | $1.86 \times 10^2$ |
| 31 | L | $3.22 \times 10^4$ | .7214 | $4.46 \times 10^4$ |
| | R | $1.76 \times 10^4$ | .7703 | $2.28 \times 10^4$ |
| Group IV: PA-gentamicin pellet | | | | |
| 32 | L | $1.58 \times 10^4$ | .7431 | $2.13 \times 10^4$ |
| | R | $2.2 \times 10^2$ | .6135 | $3.58 \times 10^2$ |
| 33 | L | $8 \times 10^1$ | .8363 | $9.56 \times 10^1$ |
| | R | $1.74 \times 10^3$ | .7555 | $2.3 \times 10^3$ |
| 34 | L | $7.8 \times 10^2$ | .3731 | $2.09 \times 10^3$ |
| | R | No growth | | |
| 35 | L | $1.22 \times 10^4$ | .3251 | $3.75 \times 10^4$ |
| | R | No growth | .3153 | — |
| 36 | L | $3.7 \times 10^3$ | .4712 | $7.85 \times 10^3$ |
| | R | $7.2 \times 10^2$ | .4098 | $1.76 \times 10^3$ |

The results in Table 1 demonstrate that the gentamicin released from the polyanhydride is considerably more effective than the gentamicin administered via a PMMA pellet.

Modifications and variations of the method and compositions of the present invention will be apparent to those skilled in the art from the foregoing detailed description of the invention. Such modifications and variations are intended to come within the scope of the appended claims.

We claim:

1. A method for delivering a bioactive molecule to bone comprising
   making a polymeric composition including as structural and functional components a polyanhydride, and
   bioactive molecules, and implanting the material in bone.

2. The method of claim 1 wherein the bioactive molecules are selected from the group consisting of antibiotics, chemotherapeutic agents, bone morphogenic factors, angiogenesis inhibitors, and bone growth factors.

3. The method of claim 1 wherein the polyanhydride is selected to degrade over a period of less than approximately a year.

4. The method of claim 1 further comprising mixing bioactive molecules with the polyanhydride and implanting the material in bone.

5. The method of claim 1 further comprising mixing filler materials with polyanhydride to increase the structural strength of the polyanhydride.

6. The method of claim 1 for treatment of tumors comprising removing tumor material and implanting the polyanhydride-bioactive molecules in place thereof.

7. The method of claim 1 further comprising mixing the polyanhydride and bioactive material with structural and adhesive materials to form a bond cement.

8. A method for delivering a bioactive molecule to bone comprising making a polyanhydride composition including as structural and functional components:
   a polyanhydride and bioactive molecules,
   in a bone cement.

* * * * *